United States Patent [19]

Andheden et al.

[11] Patent Number: 4,859,453
[45] Date of Patent: Aug. 22, 1989

[54] METHOD FOR PREVENTING MERCURY POISONING CAUSED BY DISSOLUTION OF MERCURY FROM AMALGAM FILLINGS

[76] Inventors: Sigvard Andheden, Sandskäddevägen 14, S-260 41 Nyhamnsläge; Arthur Müller, Bärnstensgatan 19, S-253 68 Helsingborg, both of Sweden

[21] Appl. No.: 246,539
[22] PCT Filed: Jan. 13, 1988
[86] PCT No.: PCT/SE88/00003
 § 371 Date: Sep. 14, 1988
 § 102(e) Date: Sep. 14, 1988
[87] PCT Pub. No.: WO88/05295
 PCT Pub. Date: Jul. 28, 1988

[30] Foreign Application Priority Data

Jan. 16, 1987 [SE] Sweden ............................ 8700157-4

[51] Int. Cl.$^4$ ................................................ A61K 7/16
[52] U.S. Cl. ......................................... 424/10; 484/49
[58] Field of Search .................................... 424/10, 49

[56] References Cited

U.S. PATENT DOCUMENTS 4,057,649 11/1977 Bensalem ........................... 426/321
4,385,892 5/1983 Sato et al. .

FOREIGN PATENT DOCUMENTS 2518566 11/1975 Fed. Rep. of Germany .

Primary Examiner—Shep K. Rose
Attorney, Agent, or Firm—Burns, Doane, Swecker & Mathis

[57] ABSTRACT

A method for preventing mercury poisoning through the dissolution of mercury in amalgam dental fillings by the use of a toothpaste including selenium iodide or components which form selenium iodide when used in at least effective quantities.

4 Claims, No Drawings

METHOD FOR PREVENTING MERCURY POISONING CAUSED BY DISSOLUTION OF MERCURY FROM AMALGAM FILLINGS

The present invention relates to a composition for preventing mercury present in amalgam fillings from passing into and poisoning the body.

Modern dental amalgam comprises an alloy of silver, tin and copper, possibly with additions of zinc, indium and/or palladium. This alloy is mixed with mercury (between 40 to 54% by weight Hg). The resultant pliable compound is then packed into dental cavities from which defective matter has been removed. The amalgam is allowed to harden over a period of from eight to twenty four hours, and when hard provides a mechanically strong filling.

It is well known that mercury is a toxic substance. The maximum permitted mercury content of air is 0.05 mg/m$^3$. Liquid mercury has a low vapour pressure and air which has a temperature of 20° C. is not saturated until levels in excess of 10 mg/m$^3$ are reached. The poison is readily absorbed by the body, via the skin, the digestive organs and the lungs. About 76% of the mercury inhaled will remain in the lungs for approximately two whole days. Mercury from the oral cavity passes readily through the cells and into the blood. Mercury also dissolves readily in the lipoids (steroles, phosphatides, cerebrosides and coratenoids). The lipoids often form surface layers in the cells and are significant to the ability of the cells to take up dissolved substances. Because of its high solubility in the lipoids, mercury will dispense readily to the brain, liver and kidneys with a half-life of between 40 and 80 days.

Tests were carried out on several people with amalgam fillings, for the purpose of measuring the amount of mercury contained by the gases of expiration. The results obtained showed that the level of mercury present exceeded the permitted level in many of the cases investigated. It has also been observed that the level of mercury concentration increases in conjunction with brushing of the teeth and chewing chewing-gum. It was found that chewing gum gave rise to a 15% increase in the mercury content. The central nerve system is the organ which is most critical with regard to the toxic effects of inhaled mercury (WHO 1976). Although elementary mercury oxidizes quickly in the blood, some of the mercury present will pass through the blood-brain-barrier before oxidation is complete. The earliest symptom at chronic low-level exposure is physiological, such as loss of memory and mental disturbances, inability to concentrate, tiredness, depression and headaches. Higher exposures result in more serious injury. Researchers are not certain of the lowest concentration at which damage is liable to be caused. According to Professor Stock (1941) symptoms of mercury poisoning are observable at levels of 10–20 ng Hg/l, while other researchers report that no symptoms could be observed at levels up to 50 ng/l. (Bull. Environ. Contam. Toxical. 1985:34,459–468)

These problems have been, and still are, the subject of lively debate. Various theories have been put forward, of which some maintain that mercury which derives from amalgam deposits is innocuous, while others maintain that there is no doubt that such deposits are the cause of many of the dental problems which have become so common today and which are often mentioned in conjunction with oral galvanism.

Four Swedish researchers, who are also dentists, have reached the conclusion that amalgam causes mercury poisoning. In one case in Östergötland, Sweden, one woman had her fillings replaced when it was established that the fillings had caused mercury poisoning. The symptoms in this case were giddiness, sore throat and cardiac problems. Another researcher in Linköping, Sweden has studied amalgam fillings in an electron microscope, and has found that amalgam fillings are not as stable as earlier believed. Mercury was found to leak constantly from the fillings examined. Droplets of mercury migrate to newly ground surfaces. After twenty four hours these droplets amalgamate to form small pools. Mercury is also released from amalgam fillings by corrosion and diffusion, although the researchers are unable to agree on the rate at which the brain and the remainder of the body are affected by this mercury.

Discussions concerning the toxicity of elementary mercury indicate that liquid mercury is relatively harmless, whereas vaporized and ionized mercury is absorbed by the various organs of the body. Experiments carried out on animals have confirmed this. In one such experiment turnips were exposed to mercury vapour and then given as food to animals. A subsequent examination of the body organs of these animals revealed the accumulation of mercury. The conclusion is drawn that elementary mercury was partially ionized in contact with the food. It is possible that similar ionization also takes place in the oral cavity of humal beings when chewing food.

It is also possible for mercury to vaporize subsequent to leaching from the amalgam. Analyses were made on the expiration air of four people whose dental fillings comprised silver-tin-amalgam. These fillings contained about 50% by weight mercury. The levels of concentration measured in each individual case were 0.1, 0.2, 1.0 and 2.1 $\mu g/m^3$. The patient from whom this latter level was measured suffered neurological ailments. These ailments disappeared after some months from removing the fillings, which indicates that the amalgam was responsible for the ailments. (Toxicology 2(1974):344–58).

It must therefore be concluded that the poisoning is caused by the mercury vapours and the ionization of elementary mercury in contact with food. The vapour is colourless and cannot be smelt and is therefore difficult to detect.

The majority of dentists do not consider alternative fillings such as plastic composites to afford the same mechanical advantages as those afforded by amalgam, e.g. small shrinkage, easily worked and easy to apply. Present day plastics are not sufficiently strong to withstand the heavy loads to which molar fillings are subjected.

These plastic compositions normally comprise two components—a synthetic resin and glass. Higher proportions of glass result in greater wear resistance. The new compositions can be cured with light. One drawback with such compositions is that they need to be completely coated with enamel on all sides. The majority of fillings, however, extend over the edges of the filled tooth towards adjacent teeth. Furthermore, chewing pressure must not be excessive. As beforementioned, the advantage of these fillings is that part of the dentist's work involving mercury is obviated, this work being the cause of increasing environmental problems.

Investigations were made at Danderyds Sjukhus (a hospital in Danderyd, a suburb of Stockholm) on enzyme activity, from which it was concluded that low enzyme activity is possibly the result of a selenium deficiency, which in turn may render one more susceptible to mercury poisoning, since selenium protects against such poisoning. The fact that selenium acts to inhibit mercury poisoning is confirmed by the results of other research, of which the following is but one example.

The interaction between selenium and mercury was investigated on mice, which showed varying quantities of $HgCl_2$ and $Na_2SeO_3$. No increase in body weight was observed when the two preparations were administered separately, although the mice to which the two compounds were given grew and developed just as well as the mice used for control purposes. On the other hand, a delay of only one hour in administering the second of the two compounds was sufficient to interrupt the detoxicating effect. This indicates that the interaction between the two compounds is at a maximum when the compounds are administered simultaneously; the interaction apparently takes place in the blood passages. (Ecotoxicol. Environ. Saf.,8(1984):6,572–80)

The interaction between mercury and selenium has also been described in another work, which comprises a review of 146 refrences describing the protective effect afforded by selenium on the toxicity of mercury on animals. Eisei Kagaku, 29(1983):4, 173–187.

This confirms the view that mercury poisoning in animals and human beings can be largely prevented by administering selenium. This is naturally due to the fact that mercury and selenium have a very high mutual reaction affinity and that they quickly form compounds when they are present in active forms. The resultant HgSe compound is higlhly stable and can only be split under special circumstances.

Accordingly, the objective of the present invention is to prevent mercury poisoning resulting from the dissolution of mercury from amalgam dental fillings.

This object is achieved with an inventive composition which is characterized by the constituents set forth in the following claims. The work on which the inventive composition is based has shown surprisingly that mercury can be bound so firmly to amalgam that no mercury will exude from the amalgam dental fillings to creat toxic conditions, by providing a selenium compound capable of forming a mercury-selenide over the amalgam surfaces while mechanically activating said surfaces.

The following can be established with regard to the selenium compound used in this case. Experiments have shown that the problems concerned cannot be solved successively by the direct application of elementary selenium. Despite the fact that free or exposed mercury surfaces were observed in the amalgam, it was not possible to form a layer of HgSe over these surfaces when using elementary selenium. Although it is possible to use organic selenium compounds, such compounds are made less suitable by the risk of forming poisonous organic mercury compounds in conjunction therewith.

Various inorganic compounds have been tested, with positive results. It is also a requirement in this instance, however, that the compound administered will not have a harmful effect on the human body.

The method used to apply the composition is also one which will ensure that no harmful substances remain in the oral cavity and that there is a possibility of mercury which may have dissolved out from the amalgam or removed therefrom by wear of entering the body. The invention also obviates the need of replacing old amalgam dental fillings in patients who have become ill as a result of the emission of mercury from such fillings.

After testing many different selenium compounds, a compound was found which satisfies the requirements of being unharmful and of binding mercury to the amalgam in a highly effective manner. This compound can be used safely to form on the surfaces of amalgam dental fillings a protective layer which will prevent further dissolution of mercury.

The selenium compound in question and which has been found particularly effective in the present context is selenium iodide - $SeJ_4$. Iodine is a product which is produced by the body itself, but in order to avoid the risk of creating excessive iodine levels all iodine which takes part in the reaction as an intermediate is removed subsequent to forming the mercury - selenide end product. The iodine released in the final stage of production is therefore removed by means of a method which will be described hereinafter. Any mercury which may have been freed from the amalgam by wear is also removed at the same time as the iodine. The selenium iodide need not be found in the coating composition from the beginning, but may also be formed during use. For example, it is possible, and even practical, to add alkali metal iodide to the substance together with $SeO_2$, wherewith the selenium iodide will form subsequent to applying the substances onto the surfaces to be treated. The alkali metal iodide used is preferably potassium iodide.

The invention is based on the assumption that the majority of people regularly brush their teeth with toothpaste. Consequently, in accordance with the inventive concept, the introduction of the inventive substance into toothpaste is considered to be the most suitable method of application so that the amalgam fillings present are treated regularly in conjunction with brushing of the teeth. The protective layer is thus most suitably applied in conjunction with brushing the teeth with a toothpaste which contains the selenium compound. After cleaning the teeth with this toothpaste, the resultant foam is carefully rinsed away from the mouth. The teeth are preferably brushed with the selenium containing toothpaste for a period of at least one minute, preferably at least two minutes.

Experiments were carried out in which selenium iodide was incorporated in commercial type toothpastes and the toothpastes brushed with a toothbrush onto amalgam samples produced for this purpose while simulating normal toothbrushing action. The experiments were carried out, in principle, by first producing amalgam test pieces. The surfaces of respective test pieces were photographed in a scanning electromicroscope and analysed - SEM. These surfaces were then brushed with toothpaste containing the selenium iodide and further analyses were made and further photographs taken in varying degrees of enlargement. The free mercury particles and large areas consisting of pure mercury could be readily seen on the SEM-photographs taken prior to treating the test pieces. The photographs taken after treatment also showed clearly that these mercury particles in the surfaces of the test pieces had been converted to mercury selenide and that the free mercury had been encapsulated. The foam engendered when brushing the amalgam test pieces was rinsed away with water and no traces of iodide or free mercury could be found in the resultant environment.

It will be understood that these ions are absorbed in the foam generated when brushing the teeth and will be entrained with the water used to rinse out the mouth.

The iodide may be supplied in safe excess quantities and the toothpastes used in the experiments contained as much as 5% by weight, with no traces of iodine or mercury being found around the filling. The advantage of this is that there is no risk of selenium iodide being administered in an overdose. Furthermore, the excess selenium iodide will guarantee that all mercury is captured.

The coating produced on the amalgam surface thus comprises the compound mercury selenide, HgSe, which is extremely difficult to split and which can cause no damage to any part of the ecological chain.

The invention will now be described with reference to a preferred embodiment thereof and also with partial reference to examples of comparison tests carried out in the laboratory.

As will be apparent from the aforegoing, the primary objective of this invention is to provide a substance which is capable of binding mercury to amalgam surfaces, so as to prevent mercury from being released and mixing with saliva. This is achieved, in accordance with the invention, by creating in the oral cavity Se-ions which are able to combine actively with the mercury released from the amalgam. In order to form these active selenium ions, attempts have been made to supply $SeJ_4$ in conjunction with brushing of the teeth. In the present case this has been achieved by mixing the compound effectively with conventional toothpaste. Comparison tests were carried out on amalgam that had not been treated with selenium iodide. The test pieces used were subsequently examined under a scanning electron microscope—SEM—and a number of photographs were taken and enlarged to varying degrees. The analyses and the phorographs both showed that a completely covering layer had been formed. The analyses also showed that the layer or coating comprised mainly selenium and mercury. Thus, it is obvious that the mercury had combined with the selenium to form a stable mercury selenide.

From a chemical aspect it is likely that the selenium iodide dissolves and that the resultant iodide ion combines with mercury to form a mercury iodide, and that this compound is then ionized to form solid mercury selenide, which bonds firmly with the amalgam surfaces.

EXAMPLE

Four dental fillings were prepared, by mixing 1.0 g of a copper-tin-silver alloy with 1.1 g mercury. The mixture contained 52.4% by weight mercury, which corresponds to the quantity used in dental amalgam. The mixture was homogenized in a vibratory mixer for 15 seconds. Subsequent to further homogenization, the mixture was pressed in an amalgam press and test pieces were produced. Surplus free metal was removed at the same time.

The test pieces were left to harden for twelve hours, after which a surface analysis was carried out in a scanning electron microscope (SEM) with suitable enlargement. The surface analysis comprised 69-70% by weight mercury. The analysis revealed free pools of practically pure mercury (98%).

The fillings, or test pieces, were then ground with a traditional dentist's grinding instrument and polished. A further analysis was made of the surface with the same degree of amplification as that used in the first analysis. This further analysis revealed mercury contents of between 65-66% and a number of pools of mercury. These fillings were then used as the subjects of further tests. Four fillings were used. Two of these fillings were used as reference objects, whereas the remaining two fillings were treated in accordance with the invention.

The reference subjects were treated with a standard toothpaste in which no additions were introduced, whereas the two remaining fillings were treated with toothpaste that contained 5% by weight $SeJ_4$ additive. The toothpaste was brushed onto the fillings, using a brush of average bristle-hardness and with the bristle interstices completely filled with toothpaste.

The froth generated by the toothpaste contained $SeJ_4$ and was a yellowish brown in colour. Subsequent to rinsing the treated amalgam surfaces in a manner normal with dental hygiene, the amalgam surfaces were analysed under a scanning electron microscope, with the same degrees of amplification as those used in the preceding analyses. The analyses carried out on the reference objects treated with a standard toothpaste showed no change in mercury content, which was still 65%, whereas in the case of the tests in which $SeJ_4$ was used in the toothpaste, the mercury content was found to be 62%. The treatment was repeated on the same material and the subsequent surface analysis showed that the $SeJ_4$-containing toothpaste had lowered the mercury content to 61%. Continued treatment resulted in insignificantly lower mercury contents, although the selenium content increased slightly. In no instance could iodide compound or free iodine be seen.

Treatment of the fillings with $SeJ_4$ turned the surfaces of the filling a light greyish colour. It was also noticed that the shining, defined contours typical of amalgam fillings were changed and converted to a more diffuse, colourless surface. The layer or coating, which is very thin and comprises HgSe, thus forms a protective covering against the leaching of mercury from amalgam dental fillings. It was also found that the surfaces of these fillings became harder when treated with selenium iodide.

We claim:

1. A method for preventing mercury poisoning caused by the dissolution of mercury in amalgam dental fillings, characterized in that the wearer forms a mercury selenide protective layer over the analgam surfaces by brushing a tooth surface with a toothpaste composition containing selenium iodide or components which are capable of forming selenium iodide when used in at least an effective quantity.

2. A method according to claim 1, characterized in that said effective quantity has a maximum value of 5% by weight.

3. A method according to claim 1, characterized in that the selenium-forming components are alkali metal iodide and selenium dioxide.

4. A method according to claim 3, characterized in that the alkali metal iodide is potassium iodide.

* * * * *